(12) United States Patent
Allen et al.

(10) Patent No.: US 9,255,194 B2
(45) Date of Patent: Feb. 9, 2016

(54) METHODS AND MATERIALS FOR DEPOLYMERIZING POLYESTERS

(71) Applicant: International Business Machines Corporation, Armonk, NY (US)

(72) Inventors: Robert D. Allen, San Jose, CA (US); Krishna M. Bajjuri, San Jose, CA (US); James L. Hedrick, Pleasanton, CA (US); Gregory Breyta, San Jose, CA (US); Carl E. Larson, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 123 days.

(21) Appl. No.: 14/054,425

(22) Filed: Oct. 15, 2013

(65) Prior Publication Data
US 2015/0105532 A1    Apr. 16, 2015

(51) Int. Cl.
C08J 11/28 (2006.01)
C07C 51/09 (2006.01)

(52) U.S. Cl.
CPC ............... *C08J 11/28* (2013.01); *C07C 51/09* (2013.01); *C08J 2367/02* (2013.01); *Y02W 30/706* (2015.05)

(58) Field of Classification Search
CPC ...... C07C 51/367; C07C 51/09; C08G 63/78; C08G 63/26; C08J 11/00; C08J 11/10; C08J 11/18; C08J 11/20; C08J 11/28; C08J 2367/02; Y02W 30/706
USPC .................. 528/305, 307, 308.3; 521/40–49.8
See application file for complete search history.

(56) References Cited

U.S. PATENT DOCUMENTS

| | | | |
|---|---|---|---|
| 3,884,850 A | 5/1975 | Ostrowski | |
| 3,907,868 A | 9/1975 | Currie et al. | |
| 4,078,143 A | 3/1978 | Malik et al. | |
| 5,395,858 A | 3/1995 | Schwartz, Jr. | |
| 5,580,905 A | 12/1996 | Schwartz, Jr. | |
| 5,869,543 A | 2/1999 | Boos et al. | |
| 6,410,607 B1 | 6/2002 | Ekart et al. | |
| 6,573,304 B1 | 6/2003 | Durand et al. | |
| 6,962,968 B2 | 11/2005 | Phelps et al. | |
| 7,053,221 B2 | 5/2006 | Hedrick et al. | |
| 2009/0287017 A1 | 11/2009 | Al Ghatta et al. | |
| 2011/0003949 A1 | 1/2011 | Hedrick et al. | |
| 2011/0004014 A1 | 1/2011 | Hedrick et al. | |
| 2011/0201848 A1 | 8/2011 | Ii et al. | |
| 2012/0223270 A1 | 9/2012 | Alabdulrahman et al. | |

FOREIGN PATENT DOCUMENTS

| | | |
|---|---|---|
| EP | 174062 A2 | 3/1986 |
| EP | 174062 A3 | 3/1986 |
| EP | 865464 B1 | 5/2001 |
| GB | 610136 | 10/1948 |
| JP | 2006232701 A | 9/2006 |
| JP | 2012072400 A | 4/2012 |
| WO | 9720886 A1 | 6/1997 |

OTHER PUBLICATIONS

Machine translation of JP2012-072400, Funatsukuri et al , Dec. 4, 2012.*
International Search Report and Written Opinion for counterpart PCT Application No. PCT/JP2014/004047, dated Oct. 28, 2014.
Acar et al., The Effect of Xylene as Aromatic Solvent to Aminoglycolysis of Post Consumer PET Bottles, Polymer Engineering Science 53(11):2429-2438 (2013).
Fukushima et al., Unexpected Efficiency of Cyclic Amidine Catalysts in Depolymerizing Poly(ethylene terephthalate), Journal of Polymer Science, Part A: Polymer Chemistry 51(7):1606-1611 (2013).
Kamimura et al., Efficient Chemical Recycling of Waste Fiber-Reinforced Plastics: Use of Reduced Amounts of Dimethylaminopyridine and Activated Charcoal for the Purification of Recovered Monomer, Journal of Material Cycles and Waste Management 12(2):93-97 (2010).
Bartolome et al., Recent Developments in the Chemical Recycling of PET, Material Recycling—Trends and Perspectives, Dr. Dimitris Achilias (Ed.), InTech (2012); available on-line at: http://www.intechopen.com/books/materialrecycling-trends-and-perspectives/recent-developments-in-the-chemical-recycling-of-pet.
Dove et al., N-Heterocyclic carbenes: Effective organic catalysts for living polymerization, Polymer 47:4018-4025 (2006).
Fukushima et al., Organocatalytic Depolymerization of Poly(ethylene terephthalate), Journal of Polymer Science, Part A: Polymer Chemistry 49:1273-1281 (2011).

(Continued)

*Primary Examiner* — Frances Tischler
(74) *Attorney, Agent, or Firm* — Karen Canaan; CanaanLaw, P.C.

(57) ABSTRACT

Provided is a method of depolymerizing polyesters from post-consumer products, such as beverage bottles, to produce a high purity reaction product. For the depolymerization reaction, the polyesters are reacted with an alcohol and an amine organocatalyst at a temperature of about 150° C. to about 250° C. In one application, the use of an organocatalyst with a boiling point significantly lower than the boiling point of the reactant alcohol allows for the ready recycling of the amine organocatalyst. In another application, performing the depolymerization reaction under pressure at a temperature above the boiling point of the alcohol allows for accelerated depolymerization rates and the recovery of the organocatalyst with no further heat input. In a further application, glycolytic depolymerization of poly(ethylene terephthalate) (PET) produces a reaction product of bis(2-hydroxyethyl)terephthalate (BHET), which may in turn be used to produce high purity beverage bottle grade PET, in a closed loop process with minimal waste.

31 Claims, 10 Drawing Sheets

(56) References Cited

OTHER PUBLICATIONS

Kamber et al., The Depolymerization of Poly(ethylene terephthalate) (PET) Using N-Heterocyclic Carbenes from Ionic Liquids, Journal of Chemical Education 87(5):519-221 (2010).

Nikje et al., PET Recycling by Diethylene Glycol—Diethanol Amine Binary Mixture and Application of Product in Rigid Polyurethane Foam Formulation, Journal of Macromolecular Science, Part A: Pure and Applied Chemistry 44:753-758 (2007).

* cited by examiner

METHODS AND MATERIALS FOR DEPOLYMERIZING POLYESTERS

TECHNICAL FIELD

The present invention relates generally to plastics recycling and more specifically to methods of depolymerizing polyesters, such as depolymerization of post-consumer poly(ethylene terephthalate) (PET) to produce purified terephthalate diester monomers, which may be used to manufacture recycled plastics.

BACKGROUND OF THE INVENTION

Environmental awareness, legislative measures, and public demand for environmental sustainability are leading to an increased interest in plastics recycling. Plastics material recycling is important for a wide number of reasons, including diminished use of petroleum resources, reduction of environmental pollution, preservation of landfill space, conservation of energy, and enhanced post-consumer reuse.

Poly(ethylene terephthalate) (PET), a thermoplastic polyester that is used in clothing fibers and fabrics, carpeting, packaging films, food containers, and beverage bottles is one of the most common post-consumer materials to exist in landfills. There are two conventional methods for processing post-consumer PET: mechanical recycling and chemical recycling.

Mechanical recycling, the most commonly practiced recycling method, produces a somewhat impure recycled material; for this reason, it is often used to form products other than beverage bottles. Mechanical recycling entails melt-processing and remolding post-consumer PET. Without rigorous sorting and cleaning of the incoming PET product, mechanical recycling produces a recycled PET product that lacks many of the desirable mechanical and optical properties of the original PET product. For example, the mechanical recycling melt process deteriorates the intrinsic viscosity of the PET. Further, any metals, dyes, and color contaminants present in the PET may carry over into the recycled product. By contrast, chemical recycling of PET can yield high quality PET via the chemical degradation of PET followed by repolymerization of the formed monomers. The quality of PET produced from chemical recycling of mixed post-consumer PET makes this recycling method suitable for the conversion of consumer waste PET products into high value post-consumer PET products.

Chemical recycling of PET involves the depolymerization of post-consumer PET into product monomers and oligomers. Catalysts used to carry out the depolymerization reactions include NaOH, KOH, Zeolite, metals and strong organic bases (such as guanidines and amidines). Because metal catalysts are non-biodegradable, they are considered pollutants and additional processing steps are required to remove the metals from the resultant monomers and/or oligomers. Further, if metal were to remain in the recycled monomers and/or oligomers, their presence would cause potential problems during the repolymerization of the monomers and/or oligomers back to PET. While strong organic bases are effective at catalyzing polyester depolymerization, they are relatively costly, not easy to recycle, can cause color formation in the product monomer, and are subject to air oxidation and neutralization by salt formation; characteristics that render strongly basic organocatalysts poor candidates for polyester depolymerization reactions. Another drawback to the use of metal-containing catalysts, or strongly basic organocatalysts, is that they saturate the ion exchange resins that may be used to remove residual traces of the PET polymerization catalysts in post-reaction purification, thus rendering the resins unusable for further purification procedures and increasing the frequency of regeneration cycles.

To date, there are no depolymerization catalysts that allow for effective and economical recycling of PET. Current initiatives in the chemical recycling of PET are focused on the following factors: environmentally safety, economic feasibility, ready recyclability, and industrial applicability.

SUMMARY OF THE INVENTION

The present invention overcomes the need in the art by providing a method comprising depolymerizing a polyester with an alcohol and an amine organocatalyst and/or carboxylic acid salt of same, wherein the amine organocatalyst and/or carboxylic acid salt has a structure selected from the group consisting of Structures 1, 2, and 3:

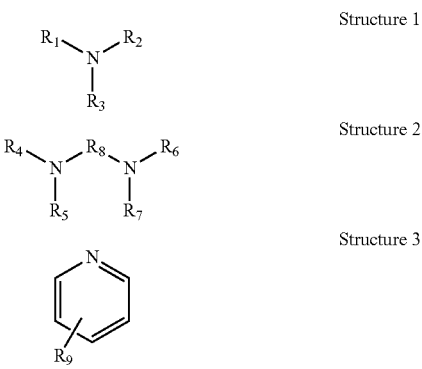

wherein, R1, R2, R3 are independently selected from the group consisting of $C_1$-$C_{10}$ alkyl, branched alkyl, cycloalkyl, alkoxy, alkylamino, and aryl; R4, R5, R6, and R7, are independently selected from the group consisting of $C_1$-$C_{10}$ alkyl, branched alkyl, cycloalkyl, alkoxy, alkylamino, and aryl; R8 is selected from the group consisting of $C_1$-$C_{10}$ alkyl, branched alkyl, and cycloalkyl; and R9 is selected from the group consisting of lower alkyl, alkoxy, and alkyl amino.

In one embodiment, R2 and R3 form a saturated or unsaturated alicyclic or aromatic ring.

In another embodiment, R1, R2, and R3 form a bicyclic ring that optionally includes one or more heteroatoms, which may be selected from the group consisting of nitrogen, oxygen, sulfur, and combinations thereof.

In a further embodiment, R4, R5, R6, and R7 form a saturated or unsaturated alicyclic or aromatic ring, and R8 is selected from the group consisting of $C_1$-$C_8$ alkyl, branched alkyl, and cycloalkyl.

In another embodiment, Structure 3 is selected from a pyridine and a pyrimidine.

In a further embodiment of the invention, the amine organocatalyst is selected from the group consisting of tetramethylethylenediamine (TMEDA); pentamethyldiethylenetriamine (PMDETA); trimethyl triaza cyclononane (TACN); triethylamine (TEA); 4-(N,N-dimethylamino)pyridine (DMAP); 1,4-diazabicyclo (2,2,2)octane (DABCO); N-methyl imidazole (NMI); and combinations thereof.

In another embodiment, the amine organocatalyst and/or carboxylic salt of same have a boiling point at least about 50° C. lower than the boiling point of the alcohol.

The present invention also provides a method comprising: depolymerizing a polyester with an alcohol and an amine organocatalyst and/or carboxylic acid salt of same in a pressure reactor at a temperature higher than the boiling point of the alcohol, wherein the amine organocatalyst and/or carboxylic salt of same has a boiling point at least about 50° C. lower than the boiling point of the alcohol (such as for example, triethylamine, TEA).

In one embodiment, the pressure of the reactor is about 10 psi to about 20 psi and the temperature is about 10° C. to about 30° C. higher than the boiling point of the alcohol.

In another embodiment, the amine organocatalyst and/or carboxylic salt of same has a boiling point at least about 100° C. lower than the boiling point of the alcohol.

The present invention further provides a method comprising: depolymerizing a polyester in a reaction mixture comprising an alcohol of 2 to 5 carbon atoms and an amine organocatalyst and/or carboxylic acid salt of same, wherein (i) the depolymerization is carried out at a pressure ranging from 0 to about 50 psi and a temperature of about 150° C. to about 250° C.; (ii) the alcohol acts as the only solvent in the reaction mixture; (iii) the amine organocatalyst and/or carboxylic salt of same has a boiling point at least about 50° C. lower than the boiling point of the alcohol; and (iv) the amine organocatalyst is present in the reaction mixture in the range of about 0.1 mol % to about 5 mol % relative to total moles of the polyester in the reaction mixture.

In one embodiment, the depolymerization is carried out at a pressure in the range of 0 to about 30 psi and a temperature in the range of about 180° C. to about 250° C.

In another embodiment, the amine organocatalyst is a tertiary amine, the alcohol is ethylene glycol, and the depolymerization is carried out at a temperature of about 150° C. to about 198° C.

In a further embodiment, the amine organocatalyst is a tertiary amine, the alcohol is ethylene glycol, and the depolymerization is carried out at a temperature of about 190° C. to about 198° C.

In another embodiment, the amine organocatalyst is a tertiary amine, the alcohol is ethylene glycol, and the depolymerization is carried out at a temperature of about 200° C. to about 250° C.

In a further embodiment of the invention, the polyester is selected from the group consisting of poly(ethylene terephthalate) (PET); poly(butylene terephthalate) (PBT); polytrimethylene terephthalate (PTT); polyethylene naphthalate (PEN); polyethylene furanoate (PEF); and combinations thereof.

In another embodiment of the invention, the alcohol is selected from the group consisting of 1,2-ethanediol (ethylene glycol); 1,3-propanediol (trimethylene glycol); 1,4-butanediol (tetramethylene glycol); 1,5-pentanediol (pentylene glycol).

In a further embodiment of the invention, the depolymerization produces a reaction product comprising a monomeric diester, the alcohol, and the amine organocatalyst.

In another embodiment of the invention, the amine organocatalyst is recycled from the reaction product by way of a distillation reaction.

In a further embodiment, the monomeric diester is repolymerized or co-polymerized with another diester and/or diacid to reproduce the polyester as a recycled product.

In another embodiment of the invention, the polyester is poly(ethylene terephthalate) (PET), the alcohol is ethylene glycol (EG), the amine organocatalyst is triethylamine (TEA), and the reaction product comprises bis(2-hydroxyethyl)terephthalate (BHET) and EG.

In a further embodiment of the invention, the BHET is purified by a method selected from the group consisting of filtration, ion exchange chromatography, decolorization, distillation, and combinations thereof.

In another embodiment of the invention, the purified BHET reaction product is repolymerized or co-polymerized with a second diester and/or diacid to form PET.

In a further embodiment of the invention, the purified BHET reaction product is repolymerized or co-polymerized with a second diester and/or diacid and one or more additional comonomers selected from the group consisting of terephthalates, diacids, diols, isophthalates, and combinations thereof. In preferred embodiments, the terephthalate is dimethyl terephthalate; the diacid is a phthalic acid, such as terephthalic acid; and the diol is cyclohexane dimethanol.

In another embodiment of the present invention, there is provided a method comprising the steps of: (a) forming a reaction mixture comprising: (i) PET; (ii) EG in an amount of about 4 to about 20 molar equivalents relative to a PET repeat unit; and (iii) a depolymerizing amine organocatalyst and/or amine salt organocatalyst; and (b) heating the reaction mixture at a temperature of about 150° C. to 250° C. to depolymerize the PET and form a terephthalate reaction product comprising BHET.

In a further embodiment of the invention, the depolymerization reactions described above are carried out in a continuous process in a continuous flow reactor vessel.

Additional aspects and embodiments of the invention will be provided, without limitation, in the detailed description of the invention that is set forth below.

DETAILED DESCRIPTION OF THE INVENTION

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

Figure 1:
FIG. 1 is a photograph of green dirty poly(ethylene terephthalate) PET flake.
Figure 2:
FIG. 2 is a photograph of clear dirty poly(ethylene terephthalate) PET flake.

As used herein, the term "clear PET flake" refers to PET obtained from clear beverage bottles and the term "green PET flake" refers to PET obtained from green beverage bottles. As is understood from those of skill in the art, post-consumer PET is typically sorted into different color fractions, including clear PET, blue PET, green PET, and amber PET. The flake derived from the post-consumer PET shares the same color as its source. Reference to "dirty" PET flake means that the beverage bottles from which the PET flake was obtained was either not subjected to washing or subjected only to minimal washing. FIG. 1 is a photograph of green dirty PET flake and FIG. 2 shows a photograph of clear dirty PET flake. As used herein the term "clean washed PET flake" means that dirty PET flake was washed and cleaned and not that the bottles from which the PET flake was obtained was washed.

Within the context of the present invention, the term "about" is used in its ordinary and customary way to indicate that numerical ranges may fluctuate beyond the ranges specified. For example, a range of about 0.1 to about 5 mol % may be expected to cover a lower end that is less than 0.1 mol %, such as for example, 0.09 mol % (or slightly lower), and an upper range that is greater than 5 mol %, such as for example, 5.1 mol % (or slightly higher). The term "at least about" is used to emphasize that the figure that follows the term specifies an upper value, but that such upper value is not set. For example, the phrase "the organocatalyst has a boiling point that is at least about 50° C. lower than the boiling point of the alcohol" means that the organocatalyst boils at a temperature that is at least 50° C. lower than boiling point of the alcohol, but that the 50° C. is not a set figure and may include a range slightly above or below the 50° C., as appropriate.

Within the context of the present invention, the terms "amine organocatalyst" and "organocatalyst" refer to amine organocatalysts and/or carboxylic salts of same. An example of an amine organocatalyst carboxylic salt is a benzoic acid salt of 1,4-diazabicyclo[2.2.2]octane. It is to be understood that within the context of the present invention, the amine organocatalysts, organocatalysts, and catalysts described herein may be used for depolymerization reactions, polymerization reactions, or both.

Within the context of the present invention, it is to be understood that in the Examples, experiments were conducted in pressure reactors and non-pressurized reactors. Where a pressure reactor was used, the reactor is specified as a "pressure reactor." By contrast, a non-pressurized reactor (such as for example, a three-neck round bottom flask) may be specified as a "reactor" (compare Examples 10 and 11). The term "reaction vessel" may refer to either a pressure reactor or a non-pressurized reactor. It is to be understood that the reactions (either pressurized or non-pressurized) described herein may include both continuous flow and batch process configurations. As used herein, the term "continuous flow reactor" refers to a reaction vessel that processes reactions in a continuous flow process. A continuous flow reactor may be either a pressurized reactor or a non-pressurized reactor.

Disclosed are methods of depolymerizing polyesters with an alcohol comprising 2 to 5 carbon atoms and an amine organocatalyst (and/or carboxylic salt of same).

The polyester starting products of the present invention may be obtained from any suitable source, including without limitation, post-consumer goods, such as beverage bottles, non-beverage containers, food containers, packaging materials, carpeting, clothing, wrapping materials, and synthetic fibers.

In preparation for the polyester depolymerization reaction, the post-consumer goods are typically shredded or pulverized into flake or other fragments, which may be used as-is without cleaning. In some cases, it may be necessary to treat the consumable goods with one or more of the following processes: pre-washing; coarse-cutting; removal of film and/or paper labels and/or cap material; wet and/or dry grinding; hot wash; caustic wash; rinsing; clean water wash; and flake sorting. The foregoing processes may be used singularly or in combination, in any order, to prepare the polyesters for the depolymerization reaction.

The polyester starting material for the depolymerization may be a homopolymer or a copolymer. Polyester homopolymers may be selected from the group consisting of linear, branched, hyperbranched, dendritic, cyclic, and star-shaped homopolymers. Polyester copolymers may be selected from the group consisting of random copolymers, block copolymers, multiblock copolymers, and alternating or random copolymers. The polyester may be in the form of a chip, flake, granule powder, particle, fiber, film, or fabric (e.g., clothing and carpet). The polyester can also contain other polymers, such as polyvinyl chloride (PVC), nylon, or, other fibers (e.g., cotton).

The most common post-consumer polyester is poly(ethylene terephthalate) (PET) (produced from polymerization of terephthalic acid and EG). The structure of a PET repeat unit is shown below.

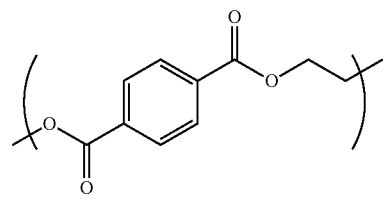

PET Repeat Unit

Other polyesters that may be depolymerized using the methods of the present invention include, without limitation, poly(butylene terephthalate) (PBT) (polymer of terephthalic acid and 1,4-butanediol); polytrimethylene terephthalate (PTT) (polymer of terephthalic acid and 1,3-propanediol); polyethylene naphthalate (PEN) (polymer of at least one naphthalene dicarboxylic acid with EG); and polyethylene furanoate (PEF) (polymer of furandicarboxylic acid with EG). Examples of other polymers that may be incorporated into terephthalate polyesters include, without limitation, poly (vinyl chloride) (PVC), nylon, and/or polylactide (PLA).

The 2 to 5 carbon alcohol used in the depolymerization reaction may be branched or non-branched. In a preferred embodiment, the alcohol is a linear glycol selected from the group consisting of 1,2-ethanediol (ethylene glycol, EG); 1,3-propanediol (trimethylene glycol); 1,4-butanediol (tetramethylene glycol); and 1,5-pentanediol (pentylene glycol or pentamethylene glycol).

The depolymerizing amine organocatalyst that may be used with the methods of the present invention are metal-free and have the general formulas of Structures 1-3

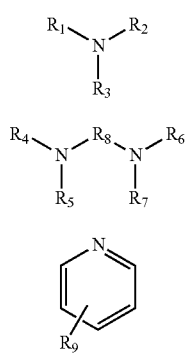

Structure 1

Structure 2

Structure 3

In one embodiment of the present invention, R1, R2, and R3 of Structure 1 are independently selected from the group consisting of $C_1$-$C_{10}$ alkyl, branched alkyl, cycloalkyl, alkoxy, alkylamino, and aryl.

In another embodiment of the present invention, R2 and R3 of Structure 1 form a saturated or unsaturated alicyclic or aromatic ring.

In a further embodiment of the present invention, R1, R2, R3 of Structure 1 form a bicyclic ring that optionally includes one or more heteroatoms, such as nitrogen, oxygen, sulfur and combinations thereof.

In another embodiment of the present invention, R4, R5, R6, and R7 of Structure 2 are independently selected from the group consisting of $C_1$-$C_{10}$ alkyl, branched alkyl, cycloalkyl, alkoxy, and alkylamino and R8 of Structure 2 is selected from the group consisting of $C_1$-$C_{10}$ alkyl, branched alkyl, and cycloalkyl.

In a further embodiment of the present invention, R4, R5, R6, and R7 of Structure 2 form a saturated or unsaturated alicyclic or aromatic ring and R8 of Structure 2 is selected from the group consisting of $C_1$-$C_8$ alkyl, branched alkyl, and cycloalkyl.

In another embodiment of the present invention, Structure 3 is a nitrogen-containing heterocyclic aromatic compound, such as a pyridine or pyrimidine, wherein R9 is selected from the group consisting of lower alkyl, alkoxy, or alkyl amino.

Examples of amine organocatalysts according to Structures 1-3 that may be used in the methods of the present invention to depolymerize polyesters include, without limitation, pentamethyldiethylenetriamine (PMDETA); trimethyl triaza cyclononane (TACN); triethylamine (TEA), 4-(N,N-dimethylamino)pyridine (DMAP); 1,4-diazabicyclo (2,2,2)octane (DABCO); tetramethylethylenediamine (TMEDA); and N-methyl imidazole (NMI).

The amine organocatalyst that may be used in the methods of the present invention preferably have a boiling point lower than that of the alcohol. In one embodiment, the amine organocatalyst has a boiling point at least about 10° C. lower than the boiling point of the alcohol. In another embodiment, the organocatalyst has a boiling point at least about 25° C. lower than that of the alcohol. In a further embodiment, the boiling point of the organocatalyst is at least about 50° C. lower than that of the alcohol. In another embodiment, the organocatalyst has a boiling point that is at least about 100° C. lower than the boiling point of the alcohol. In one example, the alcohol is ethylene glycol, which has a boiling point of approximately 198° C., and the organocatalyst is the tertiary amine organocatalyst, TEA, which has a boiling point of 89° C., which is more than 100° C. below the boiling point of the ethylene glycol (see, Examples 1-8, 10, and 11).

The amine organocatalyst may be present in the depolymerization reaction mixture in the range of up to about 0.3 molar equivalents (30 mol %) relative to the total moles of the polyester repeat units. In one embodiment, the amine organocatalyst is present in the depolymerization reaction mixture in the range of about 0.001 to about 0.1 molar equivalents (0.1 to 10 mol %). In a another embodiment, the amine organocatalyst is present in the depolymerization reaction mixture in the range of about 0.001 to about 0.05 molar equivalents (0.1 to 5 mol %). In a further embodiment, the amine organocatalyst is present in the depolymerization reaction mixture in the range of about 0.001 to about 0.01 molar equivalents (0.1 to 0.5 mol %). Examples 1-6 describe PET glycolytic depolymerization reactions that use 0.5 mol % to 5 mol % of different organocatalysts relative to the total moles of the PET.

The polyester depolymerization reactions of the present invention are preferably carried out at inert atmosphere at temperatures in the range of about 150° C. to about 250° C. and pressure ranging from 0 to about 50 psi. Reactions run at temperatures in the range of about 180° C. to about 250° C. and pressure ranging from 0 to about 30 psi may be preferred in some situations. The depolymerization step requires no additional solvent because the alcohol acts as the solvent. The reaction mixture is typically, although not necessarily, agitated (e.g., stirred, as in the Examples). Depending on the severity of contamination by insoluble materials (e.g., dirt or non-polyester fibers), the progress of the reaction can generally be monitored by visual inspection insofar as a transparent reaction mixture and/or lack of residual polyester media (e.g., flakes) indicates that all solid polyester materials have dissolved and therefore reacted. The progress of the reaction may also be monitored by standard techniques (e.g., NMR, GPC, HPLC, and IR or UV spectroscopy), by monitoring the concentration of depolymerization products (e.g., BHET).

The quality of the resultant depolymerization products can be also determined using the same standard analytic techniques.

In one embodiment, the present invention provides a method comprising: depolymerizing a polyester in a reaction mixture comprising an alcohol of 2 to 5 carbon atoms and an amine organocatalyst and/or carboxylic acid salt of same, wherein, (i) the depolymerization is carried out at a pressure ranging from 0 to about 50 psi and a temperature of about 150° C. to about 250° C.; (ii) the alcohol acts as the only solvent in the reaction mixture; (iii) the amine organocatalyst and/or carboxylic salt of same has a boiling point about 50° C. lower than the boiling point of the alcohol; and (iv) the amine organocatalyst is present in the reaction mixture in the range of about 0.1 mol % to about 5 mol % relative to total moles of the polyester in the reaction mixture. In another embodiment, the depolymerization reaction is carried out at a pressure ranging from 0 to about 30 psi and a temperature of about 180° C. to about 250° C. In a further embodiment, the amine organocatalyst is a tertiary amine, the alcohol is ethylene glycol, and the depolymerization is carried out at a temperature of about 150° C. to about 198° C. In a further embodiment, the amine organocatalyst is a tertiary amine, the alcohol is ethylene glycol, and the depolymerization is carried out at a temperature of about 190° C. to about 198° C. In a further embodiment, the amine organocatalyst is a tertiary amine, the alcohol is ethylene glycol, and the depolymerization is carried out at a temperature of about 200° C. to about 250° C.

The monomeric diester depolymerization reaction product of the present invention has the general formula of Structure 4:

Structure 4

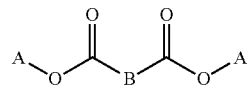

wherein each A is an independent divalent group comprising 2 to 5 carbons and B is selected from the group consisting of alkyl, cycloalkyl, aryl, and furanyl (e.g., terephthalate, napthalenedicarboxylate and furandicarboxylate). Exemplary divalent groups for the A moieties include, without limitation, ethyl, n-propyl, 2-propyl, n-butyl, iso-butyl, n-pentyl, and iso-pentyl.

In one embodiment, the monomeric diester is a monomeric dihydroxy terephthalate diester having the formula of Structure 5:

Structure 5

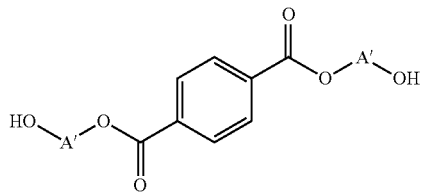

wherein each A' is an independent divalent group comprising 2 to 5 carbons. Exemplary divalent groups for the A' moieties include, without limitation, ethyl, n-propyl, 2-propyl, n-butyl, iso-butyl, n-pentyl, and iso-pentyl.

In another embodiment, the dihydroxy terephthalate diester is bis(2-hydroxyethyl)terephthalate (BHET), the latter of which has the following structure:

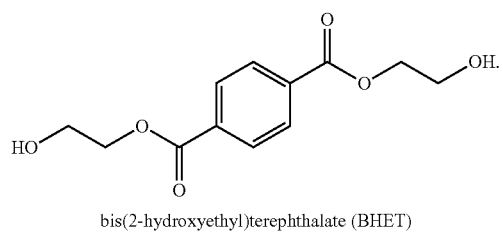 [SMILES: O=C(OCCO)c1ccc(C(=O)OCCO)cc1]

bis(2-hydroxyethyl)terephthalate (BHET)

In a preferred embodiment of the invention, the terephthalate polyester is poly(ethylene terephthalate) (PET), the glycol is ethylene glycol (EG), and the monomeric diester is BHET. The glycolytic depolymerization reaction of PET+EG+amine organocatalyst, which is used to produce BHET, is shown schematically as follows:

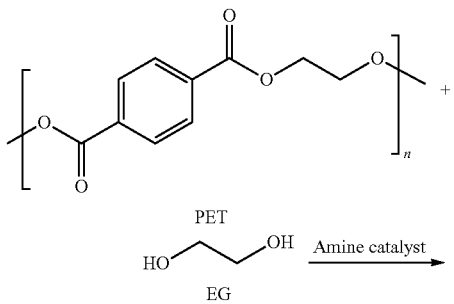

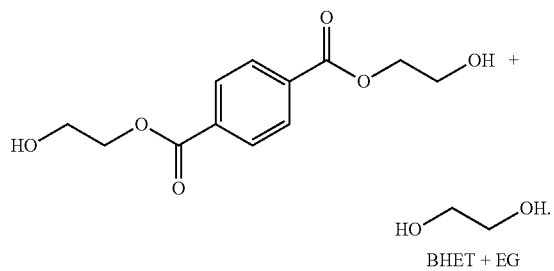

The reaction shown above depicts a method comprising the steps of: (a) forming a reaction mixture comprising: (i) PET; (ii) EG in an amount of about 4 to about 20 molar equivalents relative to a PET repeat unit; and (iii) a depolymerizing amine organocatalyst and/or amine salt organocatalyst; and (b) heating the reaction mixture at a temperature of about 150° C. to 250° C. to depolymerize the PET and form a terephthalate diester reaction product comprising BHET. Within the context of the present invention, it is to be understood that the reaction product will include alcohol (EG in the reaction above) as well as the monomeric diester (BHET in the reaction above). Further, small amounts of oligomer (e.g., dimers and/or trimers) may also be present in the reaction product; however, the quantity of the oligomer in the reaction product maybe controlled by adjusting the ratio of PET to alcohol used in the reaction. In one embodiment, the reaction mixture is heated at a temperature in the range of about 180° C. to about 250° C.

Figure 3:
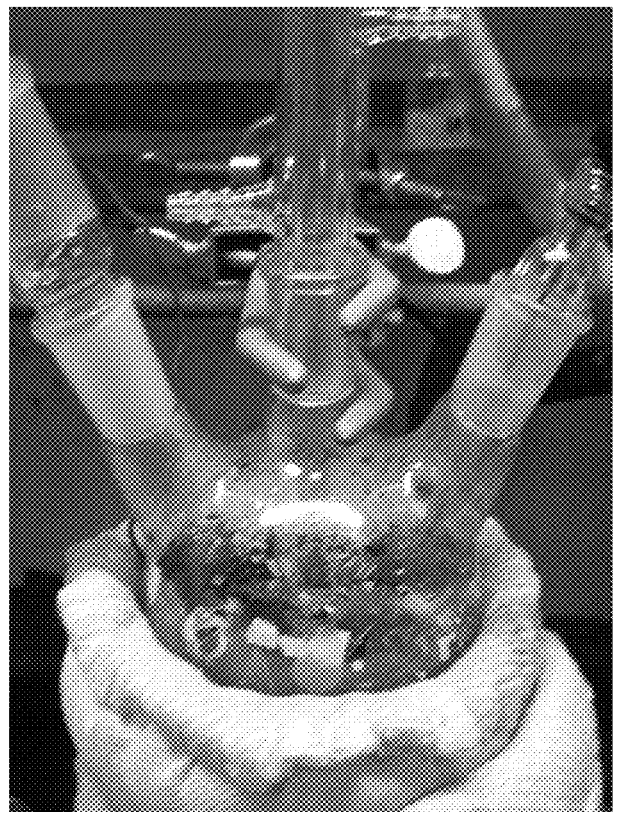
FIG. 3 is a photograph of the reaction setup of Example 2. The vessel in the photograph contained a mixture of undissolved PET prior to depolymerization.
Figure 4:
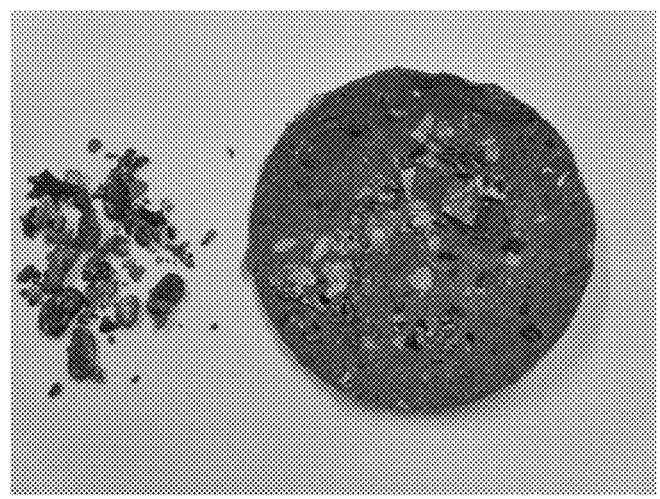
FIG. 4 is photograph of insoluble PET residue filtered from the 80° C. reaction mixture described in the Examples after completion of the glycolysis reaction.
Figure 5:
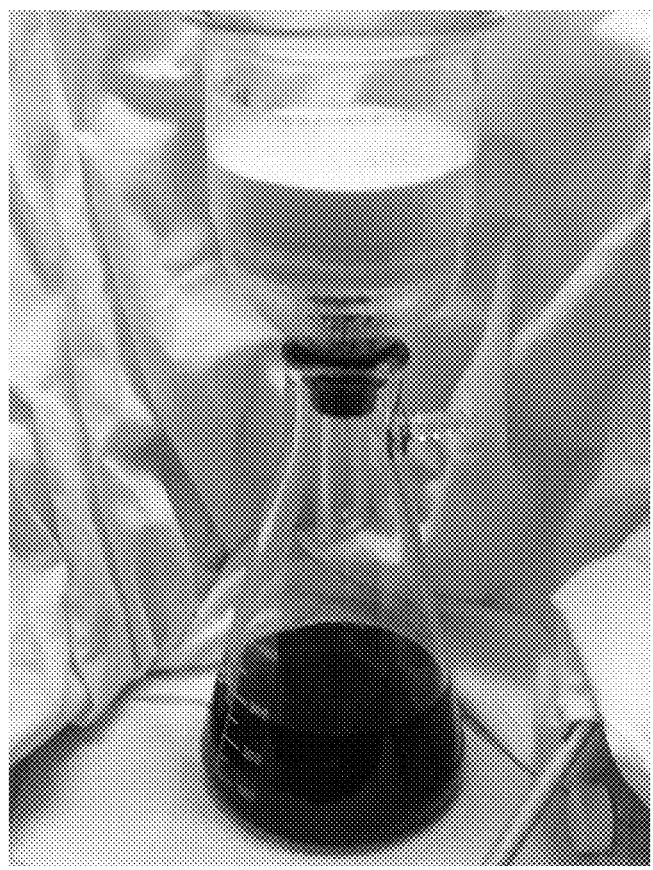
FIG. 5 is a photograph of bis(2-hydroxyethyl)terephthalate (BHET) isolated from the PET depolymerization reaction described in the Examples. Cooling of the reaction mixture resulted in crystallization of the BHET, which was isolated by direct filtration.

Examples 1, 2, 6, and 11 describe isolation of BHET from clear dirty PET flakes by way of glycolytic depolymerization with the organocatalysts PMDETA, TACN, DMAP, and TEA, respectively, in a three-neck round bottom flask under ambient pressure followed by direct filtration. FIG. 3 describes the setup for the glycolytic depolymerization step of Example 2. Examples 3 and 10 describes isolation of BHET from dirty green PET and clear dirty PET, respectively, by glycolytic depolymerization with the TEA in a pressure reactor followed by direct filtration. Examples 4, 5, and 7 describe isolation of BHET from clean washed PET flakes by glycolytic depolymerization with DABCO (Examples 4 and 7) and NMI (Example 5), in a three-neck bottom flask under pressure followed by direct filtration. FIG. 4 shows insoluble PET residue isolated from the PET by direct filtration, and FIG. 5 shows the depolymerized PET filtrate that upon solidification and filtration will form the BHET cake. As described in the Examples, following the depolymerization of the PET, the reaction mixture is cooled to ambient temperature, the BHET is allowed to precipitate as a crystalline solid, and the solid is isolated by direct filtration.

The methods described herein allow for the recovery of a high yield of monomeric diester from the crude depolymerization reaction product. Where the polyester is a terephthalate, the amount of monomeric diester (i.e., monomeric dihydroxy terephthalate diester) in the crude reaction product may range from about 90 wt % to 100 wt %, particularly 94 wt % to 100 wt %, or more particularly 96 wt % to 100 wt %, based on the weight of the crude polyester reaction product. The amount of oligomer (e.g., dimer) can be controlled somewhat by the concentration of the reactant polyester in the reactant alcohol. The depolymerization of the reactant polyester into the diester monomer and oligomer product is typically quantitative. In the terephthalate to monomeric diester depolymerization reaction described herein, the amount of terephthalate oligomers present in the crude product may range from 0 wt % to less than 10 wt %, particularly 0 wt % to 6 wt %, or more particularly 0 wt % to 4 et %, based on the weight of terephthalate reaction product. Examples 1-6 each measured crude BHET to PET oligomer at 98.5:1.5 w/w.

In one embodiment of the invention, the rate of the depolymerization reaction is accelerated by running the reaction in a pressure reactor. As is known to those of skill in the art, a pressure reactor is able to run a chemical reaction above the boiling point of a solvent. Generally, the rate of a chemical reaction roughly doubles for every 10° C. increase in the temperature of the reaction; accordingly, an advantage of raising the reaction temperature for a depolymerization reaction to a temperature of about 10° C. above the boiling point of the solvent is the shortening of the reaction time by about half. The present inventors have surprisingly and unexpectedly found that additional mild to moderate increases in both the pressure and temperature of such accelerated reactions results in further acceleration of the depolymerization reaction rate, well beyond the expected doubling rate described above. Example 10 describes an increased pressure (14-20 psi)/temperature (220° C.) PET to BHET depolymerization reaction conducted in a pressure reactor. As noted therein, the reaction was completed in 1.5 hour. By contrast, the PET to BHET reaction described in Example 11, which was conducted in a reaction vessel at ambient pressure and reduced temperature (177° C. to 179° C.), took over 11 hours for completion.

In another embodiment of the invention, the depolymerization reaction may be run as a continuous flow process in a continuous flow reactor. Using a suitable combination of variables, such as temperature and flow rate, the depolymerization reactions described herein may provide close to complete depolymerization of the polyester input during the residence time when conducted in a continuous flow reactor. For example, in the PET to BHET depolymerization reaction described herein, a slurry of pulverized PET in ethylene glycol along with an organocatalyst, such as triethylamine, is introduced into a heated continuous flow reactor with a residence time sufficient to cause depolymerization of the PET. The output of the reaction vessel is essentially crude BHET dissolved in ethylene glycol and containing the organocatalyst. The heated BHET solution may then be further processed or purified as described herein to provide BHET of sufficient purity for recycling purposes.

Importantly, the particle size of the reactant polyester input may have a significant effect on the reaction rate and the required residence time in a reaction vessel. For example, a finer particle size polyester reactant (having high surface area) will typically react faster than a polyester reactant that is a coarse particle and/or flake (having low surface area). In the case of a polyester that can form a crystalline state over the course of a reaction, such as PET, a shorter reaction time may be advantageous. The combination of small particle size of the polyester and the fast reaction time of the continuous flow process may circumvent crystalline phase formation in the polyester, thus resulting in a more efficient depolymerization reaction. Alternatively the polyester reactant may be introduced into a continuous flow reactor or a pressure reactor in its molten state where it is admixed with the alcohol and organocatalyst co-reactants and allowed to react. The combination of the molten state of the polyester and the fast reaction time of the continuous flow process may circumvent crystalline formation from the polyester, thus resulting in a more efficient depolymerization reaction.

Figure 9:
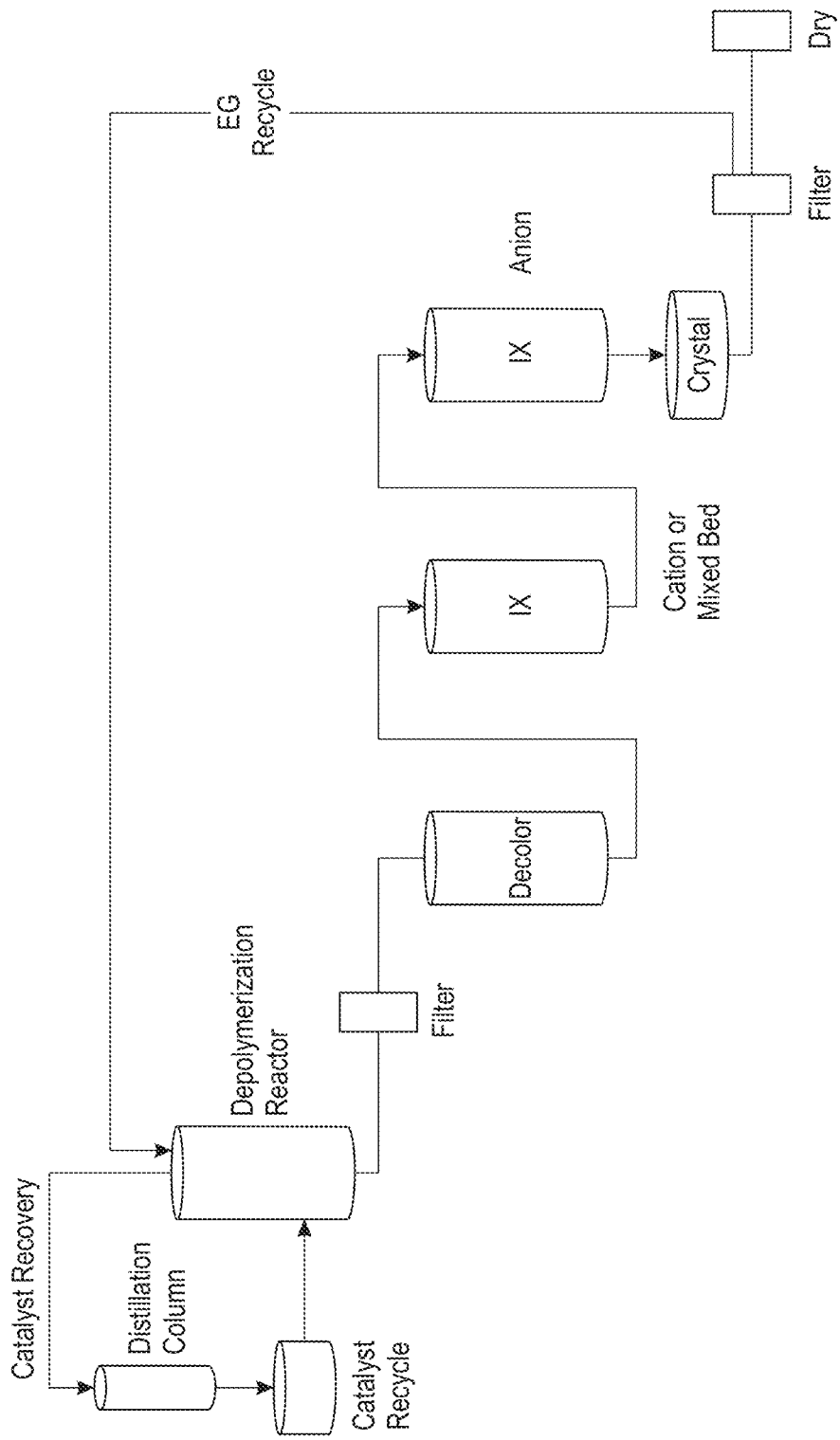
FIG. 9 is a flow chart showing the steps associated with the organocatalyst recycling and closed loop depolymerization/repolymerization methods described herein.

In another embodiment of the invention, the amine organocatalyst may be recycled by distilling the monomeric diester reaction product to produce a distillate comprising the organocatalyst (see, FIG. 9). In a preferred embodiment, the depolymerization/distillation procedure is carried out in a pressure chemical reactor or autoclave (see, Example 10); however, a pressure reactor is not necessary in order to run the distillation reaction (see, Examples 9 and 11). In one embodiment, the solvent for the depolymerization reaction is ethylene glycol, which has a boiling point of 198° C., and the reaction is run under pressure at a temperature ranging from about 200° C. to about 230° C., thus causing the depolymerization reaction to have an accelerated reaction time over the non-pressurized reaction. The large difference in volatility of the amine organocatalyst relative to the alcohol co-reactant allows for the ready recycling of the organocatalyst after depolymerization of the polyester. The lower boiling point of the amine organocatalyst relative to the higher boiling point of the alcohol allows use of the residual latent heat from the reactor or autoclave to distill off the organocatalyst by slow release of the pressure of the reaction at an elevated temperature through a condenser. The distilled organocatalyst may then be reused for subsequent depolymerization reactions. The cost savings and environmental benefits of the organocatalyst recycling method described herein are axiomatic. Example 10 describes the depolymerization of PET with EG and triethylamine (TEA) in a pressure reactor at elevated temperature (220° C.) followed by the distillation of the reaction product to yield recycled TEA. Example 9 describes the purification of BHET by short-path distillation, which was produced from PET/EG/TEA in a pressure reactor, and subsequently subjected to decolorization with activated carbon and metal removal with a cation exchange resin (as described in Examples 3 and 8). Example 11 describes the depolymerization of PET with EG and TEA carried out under ambient pressure in a non-pressurized reactor at a reduced temperature (177-179° C.) and the subsequent short-path distillation of the BHET reaction product to yield recycled TEA.

In a further embodiment, the present invention provides a method comprising: depolymerizing a polyester with an alcohol and an amine organocatalyst and/or carboxylic acid salt of same in a pressure reactor at a pressure of about 10 psi to about 20 psi and at a temperature of about 10° C. to about 30° C. higher than the boiling point of the alcohol, wherein the amine organocatalyst and/or carboxylic salt of same has a boiling point about 100° C. lower than the boiling point of the alcohol. Where the polyester is a terephthalate (such as PET), the alcohol is a glycol (such as EG), and the amine organocatalyst is a tertiary amine (such as TEA), the depolymerization reaction is carried out at a temperature of about 200° C. to about 250° C.

In the case of PET glycolysis, reaction temperatures in the region between the 70° C. Tg (glass transition temperature) and the 260° C. Tm (melting temperature) of the PET polymer may result in a phase transformation of increased crystallinity. In the Examples, it is demonstrated that the reaction of the present invention is biphasic until very near completion (e.g., solid PET flakes in liquid glycol reactant and catalyst). As described in Example 11, a longer reaction time for the depolymerization reaction resulted in increased crystallinity of the PET flakes remaining in the reaction vessel during the depolymerization reaction. While Example 11 shows that the depolymerization reaction may occur at a lower temperature (177° C. to 179° C.), the flakes remaining in the reactor during the depolymerization reaction (while smaller in size than flakes seen in the higher temperature reactions) tended to react more slowly with the EG and TEA than the flakes subjected to the higher temperature reactions; the result of the slower reaction time of the flakes is an extended depolymerization reaction time.

Upon completion of the depolymerization reaction, the monomeric diester reaction products may be subjected to any of the following additional (and optional) purification steps: direct filtration to remove foreign materials (see, Examples 1, 3, 8, and 11); treatment with activated carbon to remove additional impurities such as coloring agents and dyes (see, Example 8); and ion exchange treatment to remove catalyst residues, such as metals (see, Example 8). Additional optional distillation and crystallization steps may be used in combination with any of the foregoing. FIG. 9 provides a flow chart that shows how the foregoing optional procedures may fit into the method of the present invention.

If color remains after the depolymerization reaction, the monomeric diester may be further decolorized with an activated carbon, such as for example, activated charcoal powder (see, Example 8). The decolorization of the monomeric diester is best performed immediately after the depolymerization reaction is complete when the monomer is still in solution and the temperature of the solution is about 80° C. to about 90° C. The decolorization procedure is preferably performed in large scale by flow through a column bed of activated carbon, or the like, but can also be performed as a batch process, wherein the activated carbon and/or other decolorizing agent is subsequently filtered from the solution.

After depolymerization of the polyester, the resultant monomeric diester may contain varying amounts of impurities, including residual polymerization catalyst from the reaction that originally formed the polyester. Examples of polymerization catalysts that may be present in the monomeric diester depolymerization product include, without limitation, metal oxides and derivatives, such as antimony trioxide or acetate, titanium oxide, alkoxides or salts, and germanium dioxide. In order for the monomeric diester to be able to be transformed into a useable recycled polyester product, the polymerization catalyst residues may need to be removed. The use of cationic, anionic, chelating, or mixed-bed ion exchange resins are described in the art for removal of impurities, such as metal-containing catalysts; however, the effectiveness of the resins may be diminished by the presence of the amine organocatalyst in the depolymerization reaction product. Because the amine organocatalyst has basic properties, it may inadvertently attach, saturate, or contaminate a cation exchange resin. By removing the amine organocatalyst via distillation as described above, the regeneration lifetime of a cation exchange resin used for decontaminating monomeric diester reaction products may be greatly extended, thus adding additional cost savings to the polyester recycling method described herein. Generally, ion exchange media should be thermally stable well above the operating temperature of the process; thus, ion exchange resins used on the monomeric diester reaction products of the present invention should preferably be stable at a temperature of at least 100° C. Maintaining an efficient ion exchange resin is an important prerequisite to having a useful depolymerization reaction end product that may be used for effective recycling. Example 8 describes the batch processing decolorization and ion exchange treatment for the monomeric diester BHET.

Removal of residual polymerization catalysts from the depolymerization reaction product is also important if an additional distillation step is required for purification, since residual polymerization catalysts remaining in the reaction product may compromise the distillation process.

In another embodiment of the present invention, the polyester starting product and monomeric diester reaction product are used in a closed-loop recycling process. Under this process, the polyester is depolymerized to produce a purified monomeric diester, which in turn is repolymerized or co-polymerized to produce purified polyester, with minimal input and waste-product generation. As previously described, when the depolymerization reaction is completed, the amine organocatalyst is removed by distillation and recycled for use in a subsequent depolymerization reaction. The monomeric diester produced by the depolymerization reaction is purified by one or more of the methods previously described, including direct filtration, treatment with activated carbon, ion-exchange, distillation, and crystallization. After purification, the monomeric diester reaction product may be repolymerized or co-polymerized to reform the polyester by the removal of one equivalent of alcohol, which may be used as feedstock for subsequent depolymerization reactions. In other words, the alcohol from the repolymerization reaction may be recycled to run additional depolymerization reactions. The flowchart of FIG. 9 shows the various steps described herein for the closed loop depolymerization/repolymerization (and/or depolymerization/co-polymerization) method of the present invention, including the organocatalyst recycling procedure. The closed loop recycling method is also shown schematically below for the depolymerization/repolymerization of PET/BHET, respectively.

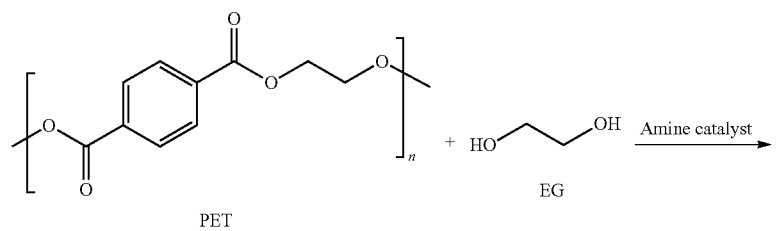

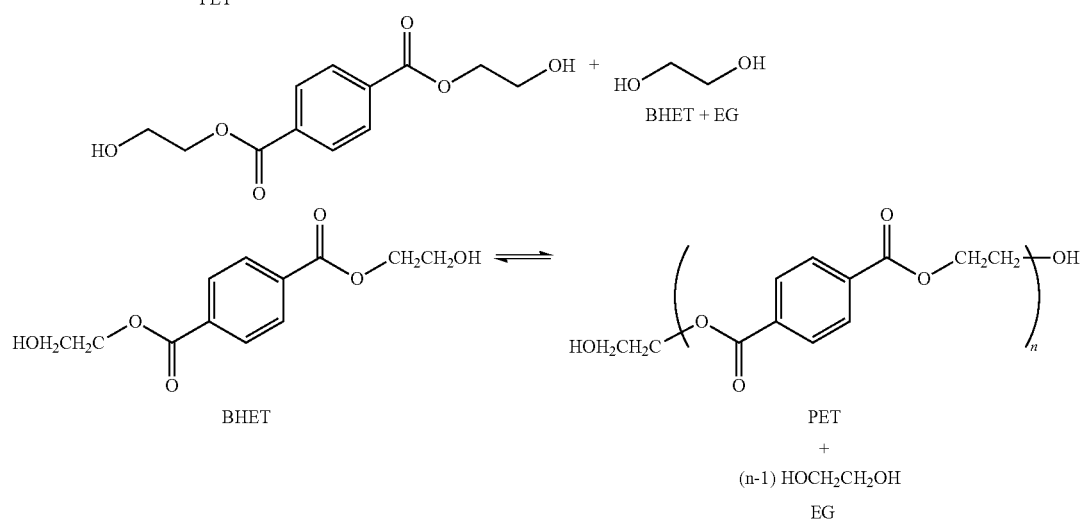

In a further embodiment of the invention, the monomeric diester to polyester repolymerization reaction is a hybrid reaction wherein the monomeric diester is repolymerized or co-polymerized with one or more additional other comonomers selected from the group consisting of terephthalates, such as dimethyl terephthalate (DMT); diacids, including phthalic acids; diols, such as cyclohexone dimethanol; isophthalates, and combinations thereof. Following is a schematic showing a repolymerization reaction of BHET to PET using the comonomers DMT and terephthalic acid (TPA).

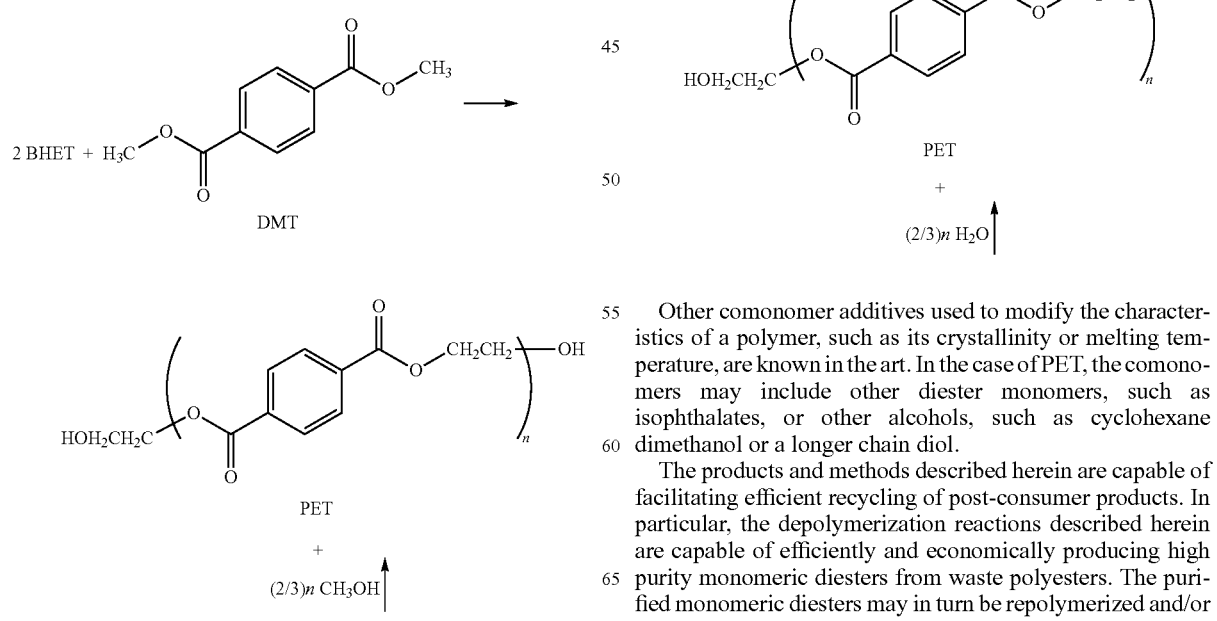

Other comonomer additives used to modify the characteristics of a polymer, such as its crystallinity or melting temperature, are known in the art. In the case of PET, the comonomers may include other diester monomers, such as isophthalates, or other alcohols, such as cyclohexane dimethanol or a longer chain diol.

The products and methods described herein are capable of facilitating efficient recycling of post-consumer products. In particular, the depolymerization reactions described herein are capable of efficiently and economically producing high purity monomeric diesters from waste polyesters. The purified monomeric diesters may in turn be repolymerized and/or co-polymerized to reform the polyesters as high grade recycled products. Further, as described above, organocatalysts used to run the depolymerization reactions and the alcohols produced from the repolymerization reactions may both be individually recycled for use in subsequent depolymerization reactions. Because the depolymerization/repolymerization (and/or depolymerization/co-polymerization) reactions described herein may be carried out in a closed loop process, the reactions are capable of producing the recycled products with minimal waste.

It is to be understood that while the invention has been described in conjunction with the embodiments set forth above, the foregoing description as well as the examples that follow are intended to illustrate and not limit the scope of the invention. Further, it is to be understood that the embodiments and examples set forth herein are not exhaustive and that modifications and variations of the invention will be apparent to those of ordinary skill in the art without departing from the scope and spirit of the invention.

All patents and publications mentioned herein are incorporated by reference in their entireties.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

The following examples describe glycolysis (i.e., glycolytic depolymerization) reactions of PET with EG and various amine organocatalysts.

Materials purchased or prepared in the following examples are listed in the Table 1. Purchased materials were used as received. Post-consumer PET was obtained from beverage bottles that were not subjected to the typical cleaning and washing processes used in mechanical PET recycling.

TABLE 1

| ABBREVIATION | DESCRIPTION | SOURCE |
|---|---|---|
| PET | Post-consumer Poly(ethylene Terephthalate), Flakes | Beverage Bottles |
| EG | Ethylene Glycol | Sigma-Aldrich |
| BHET | Bis-(Hydroxyethyl)terephthalate | Example 1 |
| PMDETA | Pentamethyldiethylenetriamine | Sigma-Aldrich |
| TACN | Trimethyl triaza cyclononane | Sigma-Aldrich |
| TEA | Triethyamine | Sigma-Aldrich |
| DMAP | 4-(N,N-Dimethylamino)pyridine | Sigma-Aldrich |
| DABCO | 1,4-Diazabicyclo (2,2,2)octane | Sigma-Aldrich |
| NMI | N-Methyl Imidazole | Sigma-Aldrich |

Example 1

Glycolysis Reaction of PET with EG and 1 mol % Pentamethyldiethylenetriamine (PMDETA)

A 500 mL three neck round-bottom flask was equipped with the following: a mechanical overhead stirrer; an air-cooled condenser; a thermocouple; a pressure equalized gas addition tube feeding nitrogen into the condenser; and a temperature-controlled heating mantle. The flask was charged with post-consumer clear dirty PET flakes (50.0 g, 0.26 mol); EG (250 g, 4.03 mol); and PMDETA (0.45 g, 0.0026 mol) (1 mol % relative to the total moles of PET) in the reaction mixture). FIG. 1 shows a photograph of clear dirty PET flakes. The flask was purged with nitrogen gas, and then heated to an internal temperature of about 190° C. and stirred at 190-198° C. until the reaction was deemed complete due to the disappearance of visible PET flakes. Next, the heating mantle was removed and the mixture was allowed to cool to 80-90° C. at which time the mixture was filtered while still hot through Whatman #2 qualitative grade filter paper to remove insoluble material. FIG. 4 shows a photograph of the insoluble PET residue filtered from the reaction mixture. As shown in FIG. 4, the insoluble PET residue consisted primarily of melted labels, miscellaneous plastic, paper pieces, fibers, and particles ("dirt"). FIG. 5 shows the BHET/EG filtrate isolated from the PET depolymerization mixture. The filtrate was allowed to cool to room temperature overnight at which time that filtrate had solidified into a mass of BHET/EG. The solidified filtrate was passed through a fritted glass filter and the solid was washed with 2×25 mL portions of EG. The resulting BHET filter cake was then dried under vacuum. After processing, aliquots of the crude product were taken for $^1$HNMR and GPC analysis in order to evaluate the content. BHET:PET oligomer 98.5:1.5 w/w.

Example 2

Glycolysis Reaction of PET with EG and of 0.5 mol % of Trimethyl Triaza Cyclononane (TACN)

The same procedure described in Example 1 was used to process the following materials: post-consumer clear dirty PET flake (50.0 g, 0.26 mol), EG (250 g, 4.03 mol), and TACN (0.22 g, 0.0013 mol) (0.5 mol % relative to the total moles of PET in the reaction mixture). After processing, aliquots of the crude product were taken for $^1$HNMR and GPC analysis in order to evaluate the content. BHET:PET oligomer 98.5:1.5 w/w. FIG. 2 shows a photograph of clear dirty PET flake and FIG. 3 shows a photograph of the reaction set-up for this example.

Example 3

Figure 6:
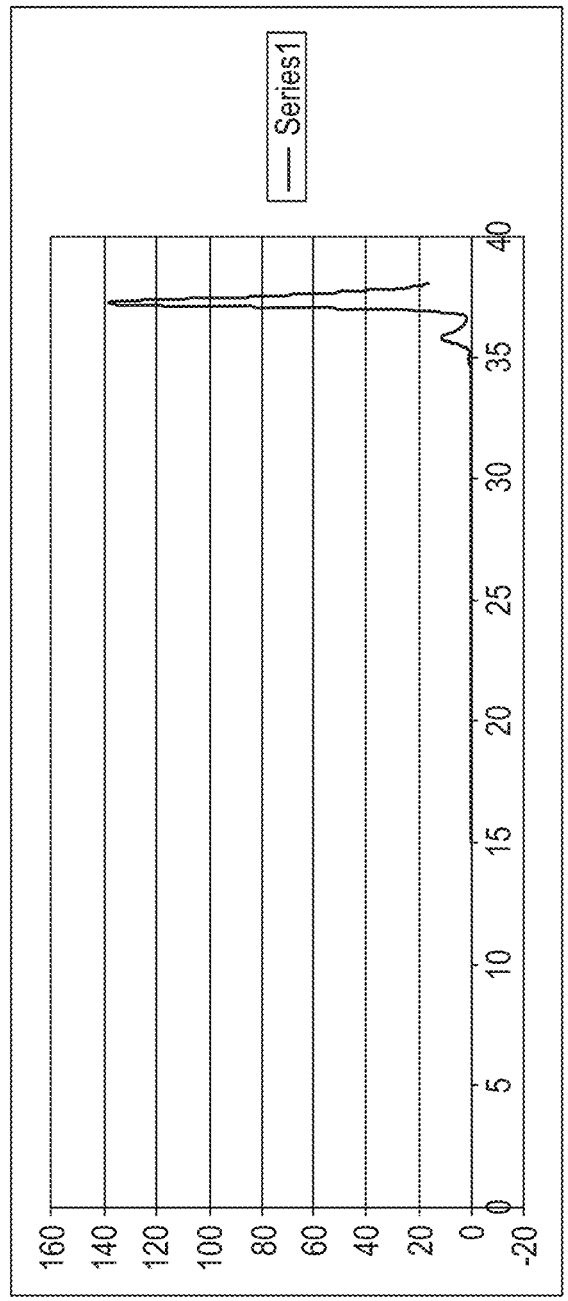
FIG. 6 is a graph of a GPC chromatogram of the crude BHET product formed in the glycolysis reaction of PET with ethylene glycol (EG) and triethylamine (TEA) organocatalyst.
Figure 7:
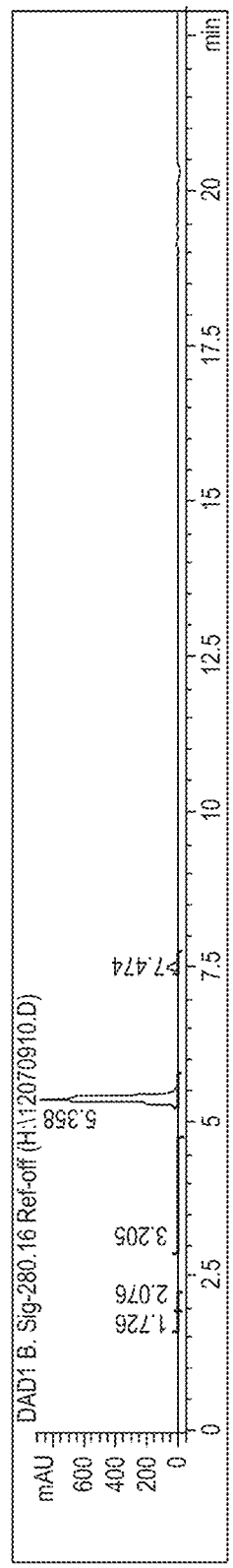
FIG. 7 is a graph of an HPLC-UV chromatogram of the crude BHET product formed in the glycolysis reaction of PET with EG and TEA organocatalyst.
Figure 8:
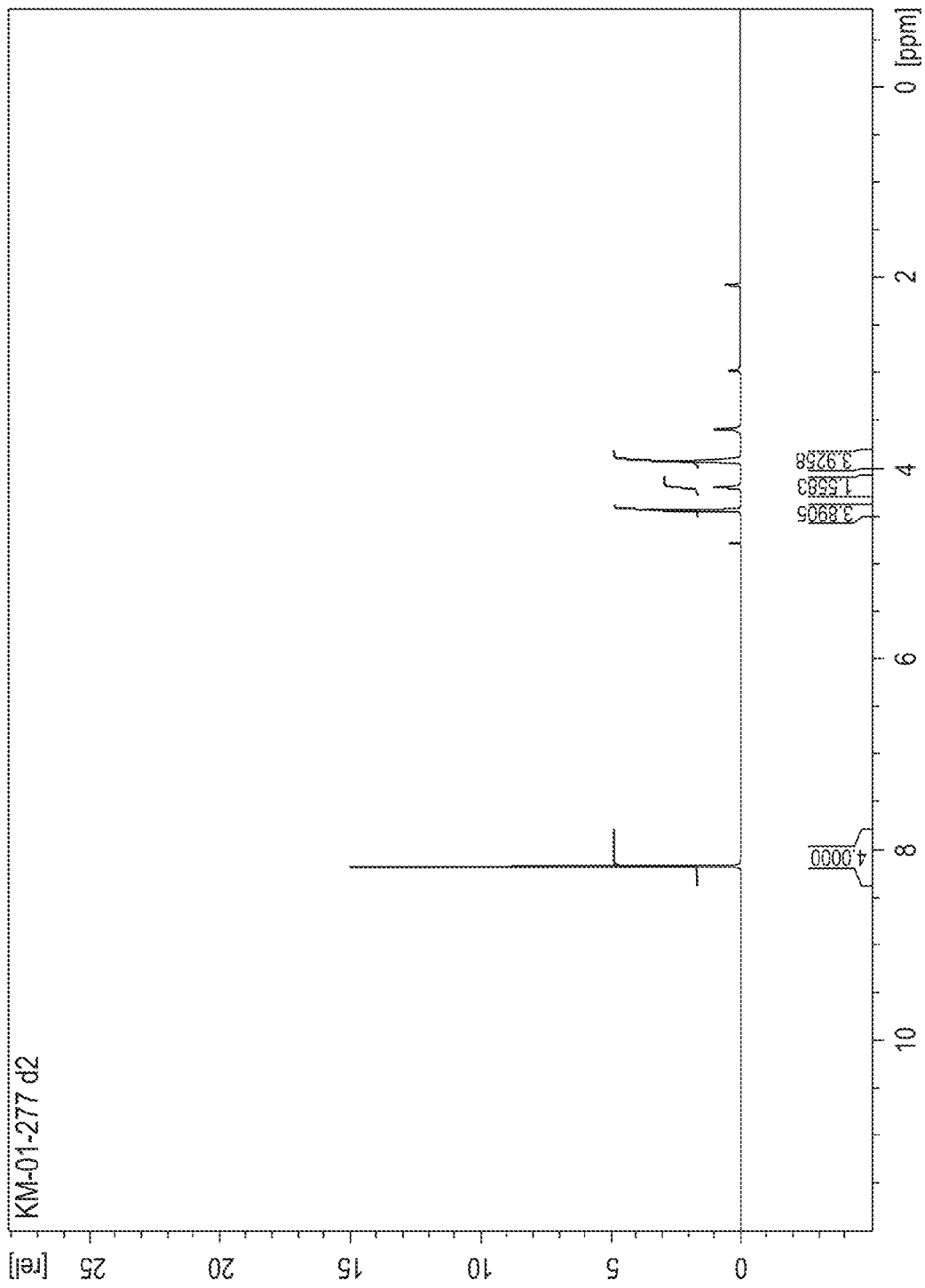
FIG. 8 is a 400 MHz $^1$H NMR spectrum of a BHET product made from green dirty PET flake with 5 mol % TEA organocatalyst.

Glycolysis Reaction of PET with EG and 5 mol % of Triethylamine (TEA) in a Pressure Reactor Post-consumer green dirty PET flake (50.0 g, 0.26 mol), EG (250 g, 4.03 mol), and 5 mol % of TEA (1.3 grams; 0.013 mol) (5 mol % relative to the total moles of PET in the reaction mixture) were placed in a Parr-Pressure reactor and purged with nitrogen. The reactor was then sealed and the reaction mixture was heated to an internal temperature of about 220° C. with stirring. At this temperature, the internal pressure was observed at about 20 psi, and the reaction was left at this temperature and pressure for 1 h at which time the heating mantle was removed, and the mixture was allowed to cool to 80-90° C. The Parr-Pressure reactor was then opened and the mixture was filtered through Whatman #2 qualitative grade filter paper while still hot to remove insoluble material. Similar to Examples 1 and 2, the insoluble PET material consisted primarily of what appeared to be melted labels, miscellaneous plastics, paper pieces, fibers, and particles ("dirt"). The weight of the recovered material was about 4-6 grams. The BHET/EG filtrate from the PET depolymerization reaction was allowed to cool to room temperature overnight at which time filtrate had solidified into a mass of BHET/EG. The solidified filtrate was passed through a fritted glass filter and the solid was washed with 2×25 mL portions of EG. The filter cake was then dried under vacuum. After processing, aliquots of the crude product were taken for $^1$HNMR and GPC analysis in order to evaluate the content. BHET:PET oligomer 98.5:1.5 w/w. FIG. 6 shows a GPC chromatogram of the crude BHET product formed from the depolymerization reaction; FIG. 7 shows a HPLC-UV chromatograph of the crude BHET product formed from the depolymerization reaction; and FIG. 8 shows an NMR spectrum of the crude BHET product formed from the depolymerization reaction.

Example 4

Glycolysis Reaction of PET with EG and 2 mol % 1,4-Diazabicyclo[2.2.2]Octane (DABCO)

The same procedure described in Example 1 was used to process the following materials: washed and clean PET flake (50.0 g, 0.26 mol), EG (250 g, 4.03 mol) and DABCO (0.58 g, 0.0052 mol) (2 mol % relative to the total moles of PET in the reaction mixture). After processing, aliquots of the crude product were taken for $^1$HNMR and GPC analysis in order to evaluate the content. BHET:PET oligomer 98.5:1.5 w/w.

Example 5

Glycolysis Reaction of PET with EG and 2 mol % of N-Methyl Imidazole (NMI)

The same procedure described in Example 1 was used to process the following materials: washed and clean PET flake (50.0 g, 0.26 mol), EG (250 g, 4.03 mol) and NMI (0.42 g, 0.0052 mol) (2 mol % relative to the total moles of PET in the reaction mixture). After processing, aliquots of the crude product were taken for $^1$HNMR and GPC analysis in order to evaluate the content. BHET:PET oligomer 98.5:1.5 w/w.

Example 6

Glycolysis Reaction of PET with EG and 1 mol % of 4-(N,N-Dimethylamino)Pyridine (DMAP)

The same procedure described in Example 1 was used to process the following materials: post-consumer clear dirty PET flake (50.0 g, 0.26 mol), EG (250 g, 4.03 mol) and DMAP (0.32 g, 0.0026 mol) (1 mol % relative to the total moles of PET in the reaction mixture). After processing, aliquots of the crude product were taken for $^1$HNMR and GPC analysis in order to evaluate the content. BHET:PET oligomer 98.5:1.5 w/w.

Example 7

Glycolysis Reaction of PET with EG and 2 mol % of 1,4-Diazabicyclo[2.2.2]Octane (DABCO) Dibenzoate A procedure similar to Example 4 was performed using the following materials: washed and clean clear PET flake (50.0 g, 0.26 mol), EG (250 g, 4.03 mol), DABCO (0.58 g, 0.0052 mol) (2 mol % relative to the total moles of PET in the reaction mixture) and Benzoic acid (1.27 g, 0.0104 mol) (4 mole % relative to the total moles of PET). The EG, DABCO and benzoic acid were first mixed together in a 500 mL 3-neck flask, purged with nitrogen, and heated to 80° C. to form DABCO dibenzoate. After stirring for 30 minutes, the PET was added and the reaction was heated to 198° C. The reaction was stopped after approximately 3.5 hours, filtered at approximately 90° C., and further cooled to recover BHET as a white solid.

Example 8

Batch Process Decolorization and Ion Exchange Treatment of BHET

The procedure of Example 3 was repeated two times resulting in the equivalent of 100 g of total depolymerized PET. The combined reaction solutions were filtered at 80-90° C. and then activated carbon (20 g) was added to the solution and stirred at 80-90° C. for 30 minutes. The heated solution was then filtered through a pad of diatomaceous earth on a fitted funnel and treated with wet Amberlyst 15 (20 g; prewashed with EG to remove impurities) with gentle agitation for 30 minutes. This resulting solution was then slowly filtered through an additional 10 g of pre-cleaned Amberlyst 15 at 80-90° C. The solution was then cooled, filtered, and dried to recover white crystals of BHET.

Example 9

Distillation of BHET

Short-path distillation of a quantity of BHET obtained from Example 8 (50 g) was performed using a Kugelrohr-type distillation apparatus at 200° C. and 100 microns Hg to obtain 42 grams of pure white BHET. The BHET was subsequently successfully repolymerized to PET.

Example 10

Glycolysis Reaction of PET with EG and 5 mol % of Triethylamine (TEA) in a Pressure Reactor with Recovery of the TEA Organocatalyst Post-consumer clear dirty PET flake (900 g, 4.68 mol) and EG (4500 g, 72.5 mol) were placed in a 2 gallon Parr-Pressure reactor and purged with nitrogen. The reactor was equipped with a stirrer, a reflux, a condenser topped with a pressure regulator, a 300 mL takeoff, a sampling valve with a receiver, a catalyst addition vessel, and a bottom take off valve for draining the reactor contents. The reactor was sealed and the reaction mixture was heated to an internal temperature of about 220° C. with stirring (200 rpm using twin blade impeller shaft) at which time the internal pressure was observed to be about ~10 psi. Next, 5 mole % of TEA (23.6 grams; 0.23 mol) (5 mol % relative to the total moles of PET in the reaction mixture) was added through the catalyst addition vessel by pressurizing the headspace above the catalyst to about 20 psi and opening the valve briefly until the pressure started to rise in the reactor upon which the valve was closed. The reaction was stirred at this temperature with the pressure between about 14 to about 20 psi pressure for 1.5 h at which time an aliquot of the reaction mixture was extracted for analysis.

Figure 10:
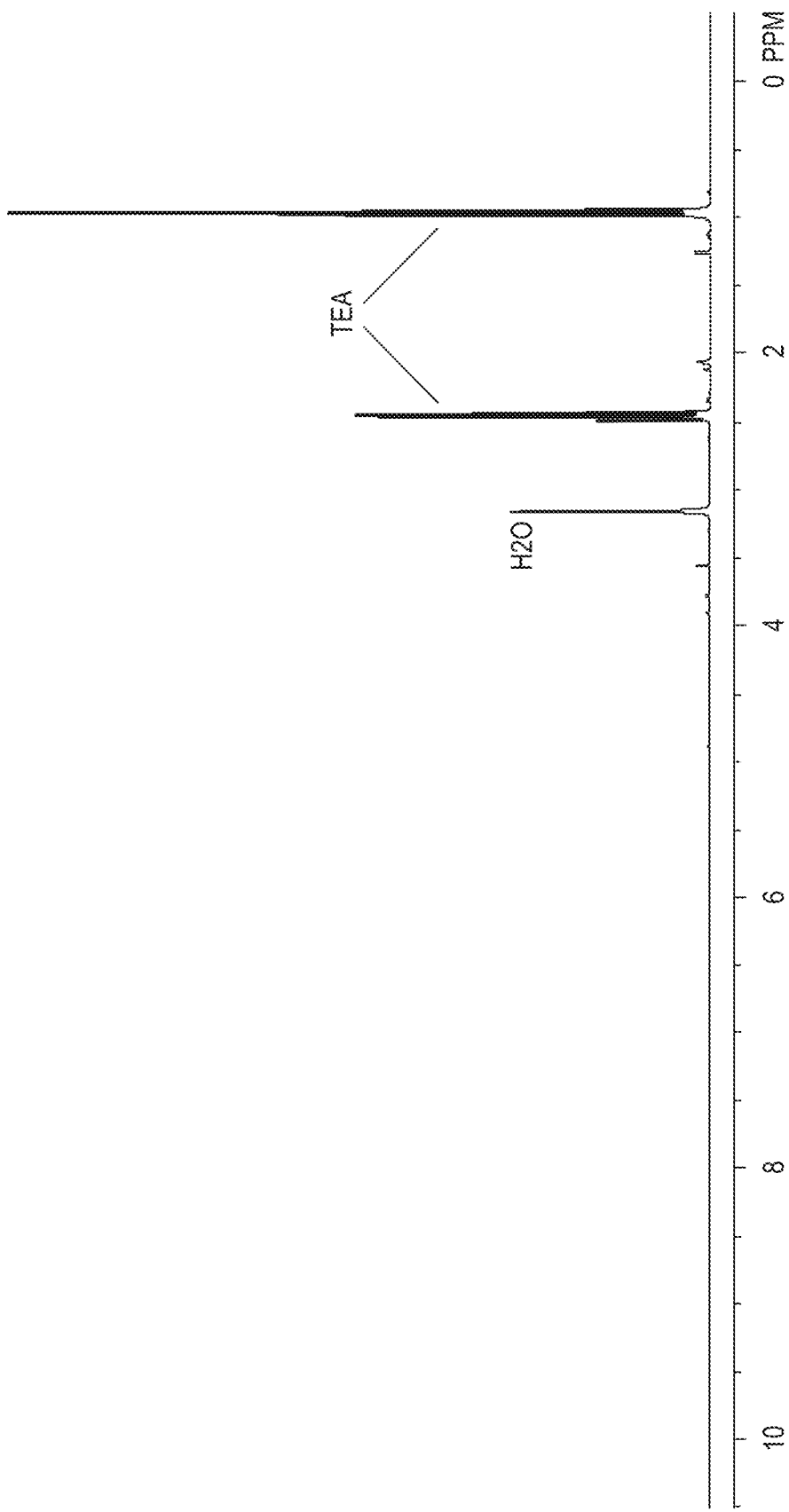
FIG. 10 is a 400 MHz $^1$H NMR spectrum of the distillate recovered at the completion of a low pressure depolymerization reaction (glycolysis of PET to BHET using 5 mole % TEA as a catalyst). The NMR shows recovery of the TEA catalyst in the distillate.

The reaction was found to be complete due to the low oligomer content of the reaction product as measured by NMR and HPLC. After completion of the reaction, the pressure of the reactor was lowered slowly through the reflux condenser regulator until ambient pressure was reached; the reactor was held at 220° C. for an additional 30 minutes to collect the distillate. H-NMR analysis showed the distillate to be mostly TEA with some water and negligible EG (FIG. 10).

Figure 11:
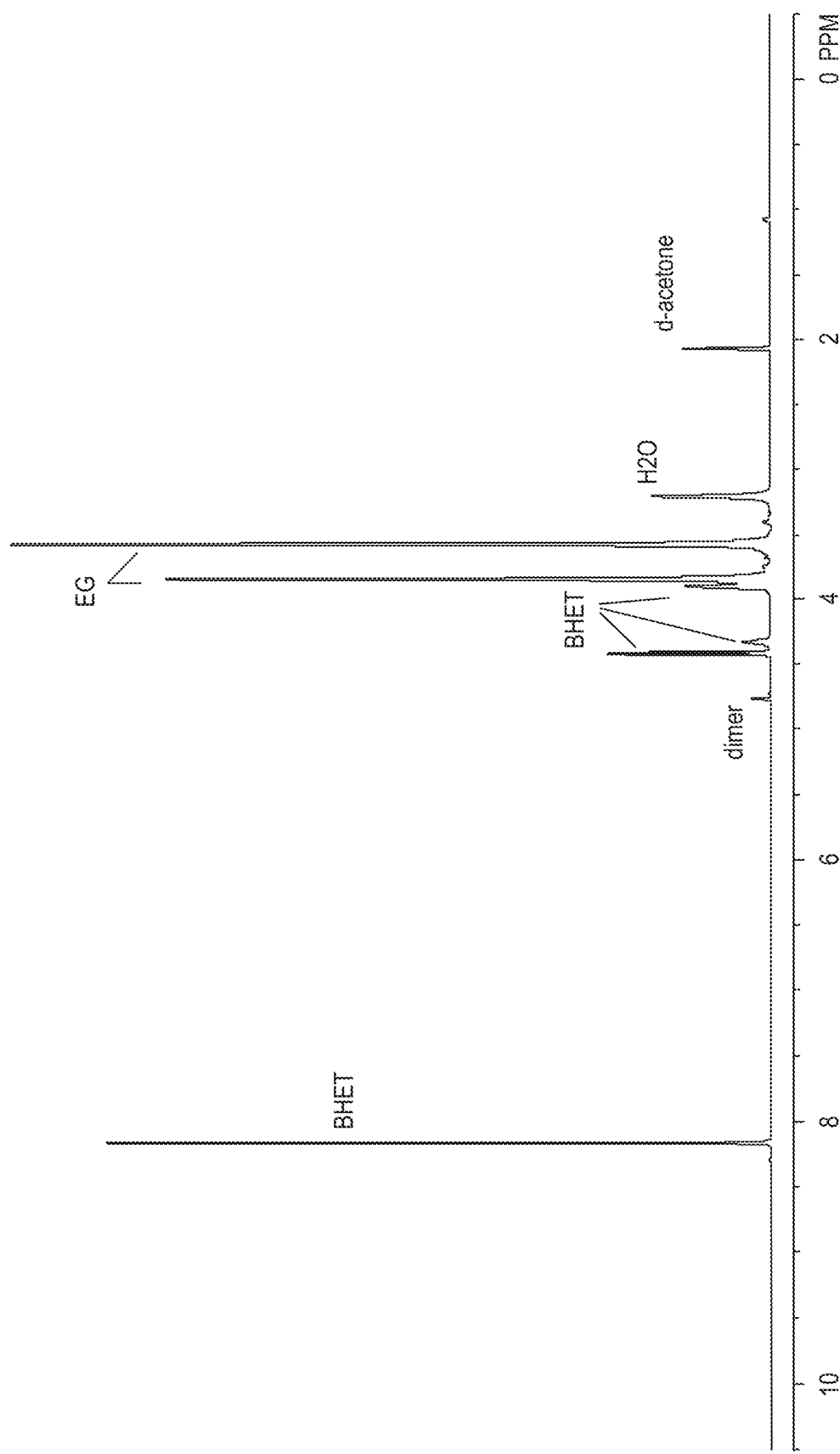
FIG. 11 is a 400 MHz $^1$H NMR spectrum of the crude BHET slurry obtained from a low pressure depolymerization reaction (glycolysis of PET to BHET using 5 mole % TEA as catalyst) after recovery of the TEA catalyst by distillation. The NMR shows that the slurry includes BHET, a small amount of oligomer, and EG.
Figure 12:
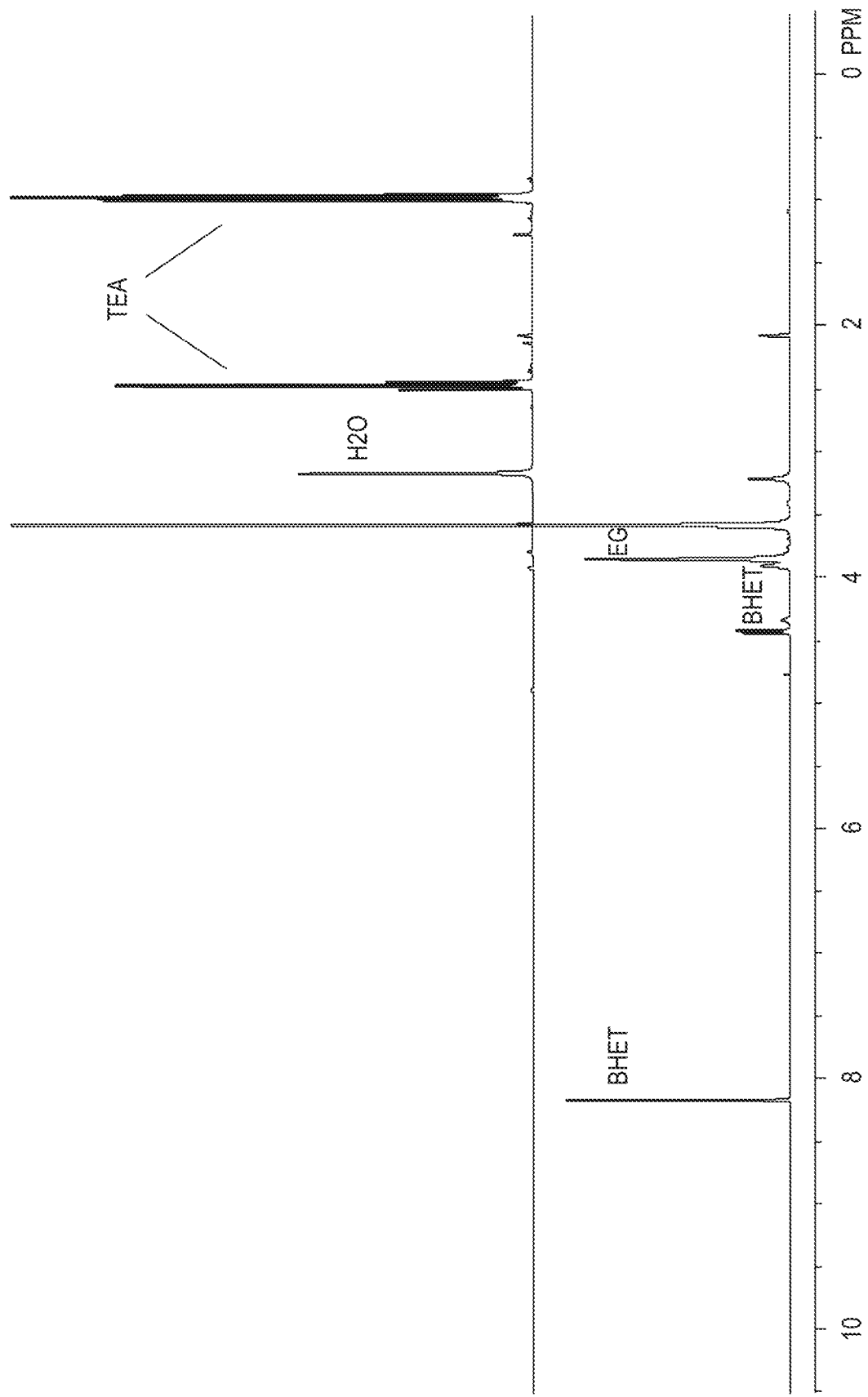
FIG. 12 is an overlay of FIG. 10 above FIG. 11 to demonstrate the absence of TEA in the BHET product slurry prior to any further purification, such as decolorization or metal removal as well as the high recovery of the TEA catalyst.

Next, the heat of the reactor was reduced and the reaction was cooled to 90° C. at which point the reaction solution was fed using low pressure (approximately 5-10 psi) to a steam-jacketed sintered glass funnel and the greyish partially slurry solution was vacuum-filtered through a pad of diatomaceous earth. After cooling the filtrate, BHET was recovered as a thick solidified white slurry in ethylene glycol; H-NMR analysis of the slurry showed low oligomer content and no traces of TEA (FIG. 11). FIG. 12 shows an overlay of FIG. 10 above FIG. 11 to demonstrate the elimination of TEA from the BHET depolymerization product slurry by simple distillation (prior to any further purification, such as decolorization or metal removal) as well as the high recovery of the TEA catalyst.

Example 11

Glycolysis Reaction of PET with EG and 5 mol % Triethylamine (TEA) at Ambient Pressure with Recovery of the TEA Organocatalyst A 250 mL three neck round-bottom flask was equipped with the following: magnetic stirrer; a water-cooled condenser; a thermocouple; a pressure equalized gas addition tube feeding nitrogen into the top of the condenser; and a temperature-controlled heating mantle. The flask was charged with post-consumer clear dirty PET flakes (40.0 g, 0.208 mol); EG (200 g, 3.2 mol); and TEA (1.05 g, 0.01 mol) (5 mol % relative to the total moles of PET in the reaction mixture). The flask was purged with nitrogen gas, and then heated to a gentle reflux with an internal temperature of about 177° C. to about 179° C. and stirred until the reaction was deemed complete due to the disappearance of visible PET flakes. It was noted that the PET flakes in the reactor, while diminishing in quantity and size, turned white as the reaction proceeded, possibly indicating crystallization, which tended to slow the reaction rate down (as determined visually by the decrease in size and amount of the visible PET flakes over time).

After 11 hours, the reaction rate, as determined by the disappearance of the remaining PET flakes, had become very slow and only a small amount of unreacted PET remained. The reactor was next fitted with a short-path distillation head and the heat input to the reactor was increased slightly to distill off the TEA catalyst. When the distillation was completed (i.e., when a small amount of distillate was collected after the vapor temperature reached 198° C. indicating mostly EG) the reaction was allowed to cool to 80-90° C. at which time the reaction mixture was filtered while still hot through Whatman #2 qualitative grade filter paper to remove insoluble material, which included a small amount of unreacted PET.

We claim:
1. A method comprising:
depolymerizing a polyester with (i) an alcohol and (ii) an amine organocatalyst and/or carboxylic acid salt of same according to Structure 1,

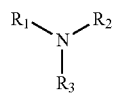

Structure 1 wherein,
R1, R2, and R3 are independently selected from the group consisting of $C_1$-$C_{10}$ alkyl, branched alkyl, cycloalkyl, and dialkylaminoalkyl, wherein R2 and R3 may form a saturated or unsaturated alicyclic ring;
carbon spacing between any two nitrogen atoms in Structure 1 is greater than one; and
the amine organocatalyst has a boiling point lower than the boiling point of the alcohol.
2. The method of claim 1, wherein the amine organocatalyst of Structure 1 is selected from the group consisting of tetramethylethylenediamine (TMEDA); pentamethyldiethylenetriamine (PMDETA); triethylamine (TEA); and combinations thereof.
3. The method of claim 1, wherein the polyester is selected from the group consisting of poly(ethylene terephthalate) (PET); poly(butylene terephthalate) (PBT); polytrimethylene terephthalate (PTT); polyethylene naphthalate (PEN); polyethylene furanoate (PEF), and combinations thereof.
4. The method of claim 1, wherein the alcohol is selected from the group consisting of 1,2-ethanediol (ethylene glycol); 1,3-propanediol (trimethylene glycol); 1,4-butanediol (tetramethylene glycol); and 1,5-pentanediol (pentylene glycol).
5. The method of claim 1, wherein the amine organocatalyst and/or carboxylic salt of same has a boiling point at least about 50° C. lower than the boiling point of the alcohol.
6. The method of claim 1, wherein the amine organocatalyst is a tertiary amine, the alcohol is ethylene glycol, and the depolymerization is carried out at a temperature of about 150° C. to about 198° C.
7. The method of claim 1, wherein the amine organocatalyst is a tertiary amine, the alcohol is ethylene glycol, and the depolymerization is carried out at a temperature of about 200° C. to about 250° C.
8. The method of claim 1, wherein the depolymerization produces a reaction product comprising a monomeric and/or oligomeric diester, the alcohol, and the amine organocatalyst.
9. The method of claim 8 wherein the amine organocatalyst is recycled as a distillate from the reaction product.
10. The method of claim 1, wherein the depolymerization reaction and one or more optional purification steps are run as a continuous flow process.
11. A method according to claim 1 comprising:
depolymerizing a polyester with (i) an alcohol and (ii) an amine organocatalyst and/or carboxylic acid salt of same in a pressure reactor at a temperature higher than the boiling point of the alcohol, wherein the amine organocatalyst has a boiling point at least about 50° C. lower than the boiling point of the alcohol.
12. The method of claim 11, wherein the pressure reactor has a pressure of about 10 psi to about 20 psi and the temperature is about 10° C. to about 30° C. higher than the boiling point of the alcohol.
13. The method of claim 11, wherein the amine organocatalyst has a boiling point of at least about 100° C. lower than the boiling point of the alcohol.
14. The method of claim 11, wherein the amine organocatalyst comprises triethylamine (TEA).
15. The method of claim 11, wherein the polyester is poly(ethylene terephthalate) (PET), the alcohol is ethylene glycol (EG), the amine organocatalyst is triethylamine (TEA), and the depolymerization reaction produces a reaction product comprising bis(2-hydroxyethyl)terephthalate (BHET) and EG.
16. The method of claim 15, wherein the BHET reaction product is purified by a method selected from the group consisting of filtration, ion exchange treatment, decolorization, distillation, and combinations thereof.

17. The method of claim 11, wherein the depolymerization reaction is run as a continuous flow process in the pressure reactor.

18. A method according to claim 1 comprising:
depolymerizing a polyester in a reaction mixture comprising (i) an alcohol of 2 to 5 carbon atoms and (ii) an amine organocatalyst and/or carboxylic acid salt of same, wherein,
(a) the depolymerization is carried out at a pressure in the range of 0 to about 50 psi and at a temperature of about 150° C. to about 250° C.;
(b) the alcohol acts as the only solvent in the reaction mixture;
(c) the amine organocatalyst and/or carboxylic salt of same has a boiling point at least about 50° C. lower than the boiling point of the alcohol; and
(d) the amine organocatalyst is present in the reaction mixture in the range of about 0.1 mol% to about 10 mol% relative to total moles of the polyester in the reaction mixture.

19. The method of claims 18, wherein the depolymerization reaction and one or more optional purification steps are run as a continuous flow process.

20. The method of claim 1, wherein the depolymerization is carried out under pressure in the range of 0 to about 50 psi and at a temperature of about 150° C. to about 250° C.

21. The method of claim 1, wherein the depolymerization is carried out under pressure in the range of about 0 to about 50 psi and at a temperature of about 200° C. to about 250° C.

22. The method of claim 1, wherein the amine organocatalyst and/or carboxylic salt of same has a boiling point of at least about 100° C. lower than the boiling point of the alcohol.

23. The method of claim 1, wherein the polyester is poly (ethylene terephthalate) (PET), the alcohol is ethylene glycol (EG), the amine organocatalyst is triethylamine (TEA), and the depolymerization is carried out at a temperature of about 200° C. to about 250° C., wherein the depolymerization produces a reaction product comprising bis(2-hydroxyethyl) terephthalate (BHET) and EG.

24. The method of claim 7, wherein the depolymerization and one or more optional purification steps are run as a continuous flow process.

25. The method of claim 8, wherein the reaction product is purified by a method selected from the group consisting of filtration, ion exchange treatment, decolorization, distillation, and combinations thereof.

26. The method of claim 10, wherein the continuous flow process is run in a pressure reactor.

27. The method of claim 19, wherein the continuous flow process is run in a pressure reactor.

28. The method of claim 8, wherein the reaction product is washed with a solvent.

29. The method of claim 28, wherein the solvent is ethylene glycol.

30. The method of claim 15, wherein the BHET reaction product is washed with a solvent.

31. The method of claim 30, wherein the solvent is ethylene glycol.

* * * * *